United States Patent [19]

Ackermann et al.

[11] 4,058,553

[45] Nov. 15, 1977

[54] METHOD OF PREPARING ALKOXYMETHYLENEMALONIC ACID ESTERS

[75] Inventors: Otto Ackermann, Troisdorf-Sieglar, Germany; Otto Bleh, deceased, late of Troisdorf-Bergheim, Germany, by Rita Bleh, legal representative; Walter Rogler, Bonn, Germany

[73] Assignee: Dynamit Nobel Aktiengesellschaft, Troisdorf, Germany

[21] Appl. No.: 582,474

[22] Filed: May 30, 1975

[30] Foreign Application Priority Data

June 4, 1974 Germany .............................. 2426964

[51] Int. Cl.² ............................................. C07C 69/66
[52] U.S. Cl. .................................................... 560/180
[58] Field of Search ..................................... 260/484 P

[56] References Cited

U.S. PATENT DOCUMENTS 3,637,812  1/1972  Tull ................................... 260/484 P Primary Examiner—Paul J. Killos
Attorney, Agent, or Firm—Burgess, Dinklage & Sprung

[57] ABSTRACT

Preparation of alkoxymethylene malonic acid ester of formula:

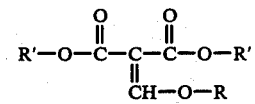

wherein R and each R' is an alkyl group, by reaction of malonic acid diester and ortho formic acid triester. The reaction is performed in the presence of a carboxylic acid or a carboxylic acid anhydride and a Lewis acid. The ortho ester is initially present in amount of at least 1,4 mols per mole of the malonic acid ester starting material. Alcohol formed during the reaction is removed during the reaction.

5 Claims, No Drawings

METHOD OF PREPARING ALKOXYMETHYLENEMALONIC ACID ESTERS

BACKGROUND

The invention relates to the preparation of alkoxymethylenemalonic acid esters by the reaction of malonic acid esters with orthoformic acid esters.

It is known that the alkoxymethylenemalonic esters are formed by the action of orthoformic acid esters on malonic acid dialkyl esters with the yielding of alcohol. The condensing agents used L. Claisen (Berichte 26, 2729 (1893), Ann. 297, 19 (1897) were acetic acid anhydride and anhydrous zinc chloride as catalysts. The reaction mechanism of this condensation was thoroughly studied by Post (J. Org. Chem. 2, 260 (1937) and Fuson (J. Org. Chem. 11, 194–8 (1946).

In the above-cited publications, approximately 2 moles of acetic acid anhydride were used per each mole of orthoester and 0.8 to 1.35 moles of malonic ester.

According to these publications, the best yields of ethoxymethylenemalonic acid diethyl ester (EMME), were 78.8% of the theory with respect to malonic acid diethyl ester, and 46% of the theory with respect to orthoformic acid ester.

Furthermore, U.S. Pat. No. 2,824,121 describes, among other things, the preparation of EMME by the reaction of malonic acid diethyl ester with orthoformic acid triethyl ester in the presence of acetic acid as the sole catalyst. It states that alkoxymethylenemalonic acid esters can be obtained with a yield of 91.8% of the theory with respect to malonic acid ester and 73.5% of the theory with respect to orthoformic acid ester, but with a transformation of only 60% of the starting substances, which it has not been possible to confirm by tests.

These known methods have considerable disadvantages. The reaction of the two components with one another is very incomplete and/or numerous by-products are formed which diminish the yield considerably. The latter are either volatile, but separable only with difficulty from EMME by distillation, such as the dialkoxymethylmalonates, for example, or they are solid, such as the pyrone derivatives which form by condensation and cyclization. This makes it very difficult in the one case and impossible in the other to produce and isolate the pure alkoxymethylenemalonic esters economically.

THE INVENTION

Surprisingly, it has been found that the disadvantages described above are avoidable, and that a nearly complete transformation to EMME is possible with a virtually complete suppression of side reaction. The subject matter of the invention is therefore a method of preparing alkoxymethylenemalonic acid esters by the reaction of malonic acid esters with orthoformic acid trialkyl esters, which is characterized in that the reaction of the malonic acid ester containing more than about 1.4 moles of the ortho esters per mole of malonic ester is performed in the presence of carboxylic acids or their anhydrides plus Lewis acids at 100° to 160° C, under pressure if desired, and the alcohol that forms during the reaction is distilled out of the equilibrium.

The transformation of the malonic ester put in is surprisingly almost complete, and 90%, by weight, of the ortho ester reacts to form EMME.

Since the malonic ester put in reacts almost quantitatively and thus disappears almost completely, the recovery and refinement of the product is quite simple.

The economy of the process is still further enhanced by the fact that the unreacted ortho ester is recovered without appreciable impurities by simple distillation and can be used in the next batch.

The orthoformic acid ester is to be present in amounts of at least about 1.4 moles per mole of malonic ester at the beginning of the reaction. Larger amounts than this can also be added advantageously, but preferably not until the reaction is in progress. Initially the ratio can best be 2.0 to 4.5, preferably about 2.5 to 4.0.

The constant and, insofar as possible, complete removal of the alcohol as it forms during the reaction is considered to be highly desirable.

It is desirable to perform the reaction with the exclusion of moisture and, in some cases, under shielding gases such as nitrogen.

The process is performed as a rule such that the mixture of malonic acid ester, orthoformic acid ester, and acid anhydride of carboxylic acid, as the case may be, is heated with stirring to ebullition in a molar ratio of 1:1.5–5:0.1–0.5.

The catalysts that can be used are particularly the low, saturated monocarboxylic and dicarboxylic acids having 1 to 5, and preferably 1 to 4 carbon atoms, and their anhydrides.

The Lewis acids which are additionally to be present, i.e., electron acceptors as defined by G. N. Lewis, are generally to be present in amounts of 0.005 to 0.05 moles per mole of carboxylic acid or carboxylic acid anhydride.

Anhydrous metal chlorides, particularly zinc chloride, in addition to aluminum chloride and iron chloride, are preferred as Lewis acids.

The products generally have the same alkyl radicals in the alkoxy group and in the alcohol radical of the ester group, these groups being preferably those of 1 to 4 carbon atoms, and most preferably the ethyl and methyl group, and in special cases still other radicals may be contained therein with similar success.

In the new process, the formation of undesired by-products is surprisingly almost completely forestalled by the excess of orthoformic acid ester and by the continuous removal of the alcohol that forms. For it has been found that the ortho ester present in excess suppresses the formation of by-products and thus eliminates one of the causes of diminished yields. Furthermore, the precise maintenance of the reaction conditions as given in the examples is desirable.

At temperatures above 160° C, very great amounts of undesired compounds form, some of them solid, which greatly reduce the yield. At low temperatures only a small transformation takes place, or products form which reduce the yield and make the economical isolation of the pure alkoxymethylenemalonic acid esters very difficult or impossible.

By increasing the amount of catalyst the reaction time can be shortened but the yield is poorer, while a reduction in the amount of catalyst considerably lengthens the reaction time for the same yield. Varying in the molar ratio of the two catalysts likewise results in a lower yield of alkoxymethylenemalonic acid esters.

The process can be performed, for example, in a reaction flask equipped with a mechanical stirrer, a means of measuring the temperature of the reaction solution, a dropping funnel and a fractionating column with condenser, reflux divider and a flask for collecting the alcohol.

The alcohol that forms is continuously distilled from the reaction mixture through the column. During the reaction time, totaling up to 12, e.g., about 3 to 12 hours, the same amount to twice the amount of acetic acid anhydride present initially can additionally be fed into the boiling reaction mixture.

The heating is regulated such that the temperature of the reaction mixture during the production of ethoxymethylenemalonic acid diethyl ester is preferably between 130° and 160° C, and at the top of the condenser the temperature is between 74° and 79° C. In the preparation of methoxymethylenemalonic acid dimethyl ester, the reaction temperature of the mixture is preferably between 110° and 160° C. After the end of the reaction the unreacted orthoformic acid ester is removed by distillation at reduced pressure, and is fed into the next batch. The alkoxymethlenemalonic acid ester remaining in the sump is evaporated from the residue at 0.01 to 0.2 Torr.

As it can be seen, a simple distillation is all that is required for the recovery of the pure product, which contributes to the good, economical performance of the process, and permits the use of very simple apparatus.

The alkoxymethylemalonic acid esters prepared are mainly intermediates, for example for the preparation of substituted methylenemalonic ester derivatives such as methylpyridylmethylenemalonic acid diethyl ester, anilinomethylenemalonic ester and others, which end products have well known uses.

EXAMPLE 1

The reaction flask is charged with 1300 parts (8.8 moles) of orthoformic acid triethyl ester, 480 parts (3 moles) of malonic acid diethyl ester, 10 parts (0.1 mole) of acetic acid anhydride and 0.1 part (0.00074 mole) of zinc chloride. This mixture is heated with strong stirring, to ebullition. At a sump temperature of 140° C, alcohol begins to distill out through the top of the column. During the course of the reaction, approximately 21 parts (0.2 mole) of acetic acid anhydride are fed in continuously, and the heating of the reaction mixture and the rate of refluxing is regulated such that the temperature at the top of the condenser is between 75° and 79° C. The condensed distillate is collected and consists substantially of ethanol, acetic acid ethyl ester, formic acid ethyl ester and small amounts of orthoformic acid ethyl ester (TEOF). During the reaction the sump temperature rises slowly to 156°–150° C. After 3 hours the reaction has ended. The unreacted orthoformic acid triethyl ester (831 parts) is distilled through the column and recycled with the next batch. Then the ethoxymethylenemalonic acid diethyl ester, freed from the zinc chloride, is removed from the residue through a simple distillation bridge in a refining vacuum at 0.1 Torr. In this manner, 608 parts of EMME are obtained. The yield is 94% of the theory with respect to malonic acid ester, and 89% of the theory with respect to TEOF.

EXAMPLE 2

370 parts (2.5 moles) of orthoformic acid triethyl ester, 197 parts (1.25 moles) of malonic acid diethyl ester, 7 parts of acetic acid anhydride and 335 mg of zinc chloride are combined in the reactor and heated to ebullition. A boiling point of 145° C establishes itself in the sump at the beginning, and one of 74° C at the top. Over a period of 3 hours, 84 parts of orthoformic acid triethyl ester and 10 parts of acetic acid anhydride are fed in. While the sump temperature is increasing in this period to 159° C, 148 g of head product is drawn off.

The refinement of the sump product is the same as in Example 1, 257 g of orthoformic acid triethyl ester and 248 g of EMME being obtained. This corresponds to an EMME yield of 87% with respect to the orthoformic acid ester and of 93% of the theory with respect to the malonic acid ester.

EXAMPLE 3

1300 parts of orthoformic acid triethyl ester, 480 parts of malonic acid diethyl ester, 10 parts of propionic acid anhydride and 0.2 parts of zinc chloride are brought to ebullition in the flask with strong stirring. Over the course of the reaction an additional 24 parts of propionic acid anhydride are fed in an ethanol is distilled out from the top of the column, the sump temperature rising to 150° C. After 3½ hours the reaction has ended. The unreacted orthoformic acid triethyl ester (835 parts) is distilled out through the top of the column at reduced pressure (5 Torr) and fed back to the next batch. After the separation of the zinc chloride, 603 parts of ethoxymethylenemalonic acid diethyl ester are separated from the residue (22 parts) by evaporation in the refining vacuum at about 0.1 Torr. The yield is 93% of the theory with respect to malonic acid diethyl ester, and 90% of the theory with respect to orthoformic acid ester.

EXAMPLE 4

1300 parts of orthoformic acid triethyl ester, 480 parts of malonic acid diethyl ester, 40 parts of succinic acid anhydride and 0.3 parts of zinc chloride are brought to ebullition in the flask with strong stirring. During the reaction, ethanol is distilled out through the top of the column, the temperature increasing over a period of 5 hours to 160° C. After the reaction has ended, refinement is performed as described in Example 3. In the refining vacuum, at about 0.3 Torr, 746 parts of product containing 583 parts of ethoxymethylenemalonic acid diethyl ester are distilled out through a distillation bridge. This corresponds to a yield of 90% of the theory with respect to malonic acid diethyl ester.

EXAMPLE 5

1300 parts of orthoformic acid triethyl ester, 480 parts of malonic acid diethyl ester, 10 parts of acetic acid and 0.2 parts of zinc chloride are heated to ebullition in a flask with vigorous stirring. While the reaction is taking place, 15 parts of additional acetic acid are added and the alcohol forming during the reaction is removed by distillation through the top of the column, the sump temperature rising to 158° C. 24 hours later the reaction has ended. The unreacted orthoformic acid triethyl ester is removed by distillation at about 5 Torr.

After separation of the zinc chloride, 596 parts of ethoxymethylenemalonic acid diethyl ester are separated from the residue through a distillation bridge in a refining vacuum of 0.1 Torr. The yield amounts to 92% of the theory with respect to malonic acid diethyl ester, and 86% of the theory with respect to orthoformic acid triethyl ester.

EXAMPLE 6

1300 parts of orthoformic acid triethyl ester, 480 parts of malonic acid diethyl ester, 15 parts of propionic acid and 0.3 parts of zinc chloride are heated to ebullition with vigorous stirring. During the reaction another 20 parts of propionic acid are added through the dropping funnel and the ethanol that forms in the reaction is removed by distillation. After 4 hours of reaction time the refining is performed as described in Example 5. The yield of ethoxymethylenemalonic acid diethyl ester is 91% of the theory with respect to malonic acid diethyl ester and 87% with respect to orthoformic acid triethyl ester.

EXAMPLE 7

1300 parts of orthoformic acid triethyl ester, 480 parts of malonic acid diethyl ester, 15 parts of acetic acid anhydride and 0.4 parts of aluminum chloride are brought to ebullition with vigorous stirring. During the reaction another 25 parts of acetic acid anhydride are added and the ethanol that forms is removed by distillation through the top of the column. After 4 hours of reaction time the reaction has ended. The processing of the product is performed as in Example 1. After refinement by distillation the yield of ethoxymethylemalonic acid diethyl ester amounts to 89% with respect to malonic acid diethyl ester and 85% of the theory with respect to orthoformic acid triethyl ester.

EXAMPLE 8

1300 parts of orthoformic acid triethyl ester, 480 parts of malonic acid diethyl ester, 15 parts of acetic acid anhydride and 0.5 parts of $FeCl_3$ are brought to ebullition with vigorous stirring. During the reaction another 25 parts of acetic acid anhydride are added, and the ethanol that forms is removed by distillation from the top of the column. After 5¼ hours of reaction time the reaction has ended. The separation of the product is accomplished as described in Example 1. The yield of ethoxymethylenemalonic acid diethyl ester is 88% of the theory with respect to malonic acid diethyl ester and 84% of the theory with respect to orthoformic acid triethyl ester.

EXAMPLE 9

265 parts (2.5 moles) of orthoformic acid trimethyl ester, 132 parts (1 mole) of malonic acid dimethyl ester, 5 parts of acetic acid anhydride and 0.375 parts of zinc chloride are combined in the reaction vessel and heated to ebullition. During the reaction an additional 7.5 parts of acetic acid anhydride are added, drop by drop, and the alcohol that forms during the reaction is removed by distillation from the top of a column (62°-66° C), while the sump temperature increases from 104° to 130° C. After the removal of 148 parts of orthoformic acid trimethyl ester by distillation, 130 parts of methoxymethylenemalonic acid dimethyl ester (94% pure) are removed by evaporation. The yield is 70% with respect to malonic acid dimethyl ester and 68% with respect to orthoformic acid trimethyl ester.

EXAMPLE 10

954 parts (9 moles) of orthoformic acid trimethyl ester, 318 parts (3 moles) of malonic acid dimethyl ester, 15 parts of acetic acid anhydride and 0.4 parts of zinc chloride are heated in a pressure apparatus under about 2 atmospheres excess pressure, at ebullition. During the reaction another 25 parts of acetic acid anhydride are added. 252 parts of methanol and easily boiling components are distilled out through the top of the column at a head temperature of 92°-94° C. The sump temperature rises from 120° to 145° C over a period of 4 to 5 hours. After the end of the reaction, 624 parts of orthoformic acid trimethyl ester are removed by distillation at reduced pressure, and after the zinc chloride has been removed by filtration, 450 parts of methoxymethylenemalonic acid dimethyl ester are then removed by evaporation. The yield amounts to 86% of the theory with respect to the input malonic acid dimethyl ester and about 83% of the theory with respect to the orthoformic acid trimethyl ester.

What is claimed is:

1. Process for the preparation of alkoxymethylene malonic acid ester by the reaction of malonic acid ester with orthoformic acid trialkyl ester, characterized in that malonic acid ester is contacted with the ortho ester in the presence of at least one of carboxylic acid and carboxylic acid anhydride, and a Lewis acid at 100°-160° C for a time sufficient for formation of the alkoxymethylene melonic acid ester, wherein the amount of ortho ester present at the beginning of the reaction is at least 1.4 moles thereof per mol of the malonic acid ester starting material, and wherein alcohol formed during the reaction is removed during the reaction.

2. Process of claim 1, wherein additional ortho ester is added during the reaction.

3. Process of claim 1, wherein the malonic acid ester starting material is an ester of an alkanol of 1-4 carbon atoms, and the ortho ester is an ester of an alkanol of 1-4 carbon atoms.

4. Process according to claim 1, wherein carboxylic acid or carboxylic acid anhydride is present initially and additional carboxylic acid or carboxylic acid anhydride is added during the reaction.

5. Process according to claim 1, wherein additional ortho ester is added during the reaction, and the malonic acid ester starting material is an ester of an alkanol of 1-4 carbon atoms, and the ortho ester is an ester of an alkanol of 1-4 carbon atoms and carboxylic acid or carboxylic acid anhydride is present initially and additional carboxylic acid or carboxylic acid anhydride is added during the reaction.

* * * * *

UNITED STATES PATENT AND TRADEMARK OFFICE
CERTIFICATE OF CORRECTION

PATENT NO. : 4,058,553
DATED : November 15, 1977
INVENTOR(S) : Otto Ackermann et al.

It is certified that error appears in the above-identified patent and that said Letters Patent are hereby corrected as shown below:

Column 4, line 20, change "150°" to ---"158°"---

Signed and Sealed this

Eighteenth Day of April 1978

[SEAL]

Attest:

RUTH C. MASON
Attesting Officer

LUTRELLE F. PARKER
Acting Commissioner of Patents and Trademarks